United States Patent [19]

Trees

[11] Patent Number: Plant 7,610

[45] Date of Patent: Jul. 30, 1991

[54] VARIETY OF GERANIUM NAMED SALMON SATISFACTION

[75] Inventor: Scott C. Trees, Elburn, Ill.

[73] Assignee: Geo. I. Ball, Inc., West Chicago, Ill.

[21] Appl. No.: 519,300

[22] Filed: May 4, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb,Burden, Ziesenheim & Webb

[57] ABSTRACT

A new cultivar is characterized by its lasting quality, free and early flowering, basal branching and vigorous upright habit. The bloom color is different from those currently available being a more delicate salmon color. The compact bush habit provides an abundance of cuttings. The bloom contrasts nicely with the medium green foliage.

1 Drawing Sheet

BACKGROUND OF THE INVENTION

The present invention comprises a new and distinct cultivar of the *Pelargonium×hortorum* known by the varietal name Salmon Satisfaction (Oglevee No. 1151, PAS No. GR-159A/85). The new variety was discovered in a selective breeding program by Mr. Scott Trees in April of 1985 in West Chicago, Ill. The new variety is a selection from the crossing of a single Salmon from $F_2$ Morgengrus by Erplog.

The new variety was first asexually reproduced by cuttings at Pan American Seed company in West Chicago, Ill. following its discovery. The new variety has been repeatedly asexually reproduced by cuttings at Oglevee Ltd. in Connellsville, PA over a several year period. It has also been trial and field tested at connellsville during the summers of 1987, 1988 and 1989 and has been found to retain its distinctive characteristics through successive propagations.

The new variety has a bloom color which is different than those currently available in this color class being a more delicate salmon color against a contrasting medium green foliage.

The new cultivar when grown in a glass greenhouse in Connellsville, PA using natural light and 60° F. (night), 68° F. (day), and 71° F. (vent) has a response time of 6 weeks from a rooted cutting to flowering in a 10 centimeter pot. This response time has determined on plants grown in a soilless media employing constant fertilizer of 200 to 250 parts per million of nitrogen and potassium and in full light. The rooted cuttings were potted Aug. 1, 1989 and flowered Sep. 15, 1989.

DESCRIPTION OF THE DRAWING

FIG. 1 of the accompanying photographic drawing illustrates the new cultivar, the color being as nearly true as possible with color illustration of this type.

DESCRIPTION OF THE NEW PLANT

The following detailed description sets forth the characteristics of the new cultivar. The data which define these characteristics were collected by asexual reproductions carried out by the Oglevee Ltd. in Connellsville, PA. The plant history was taken on six week plants blossomed under natural light in a greenhouse and color readings were taken indoors under 200–220 foot candles of cool, white fluorescent light. Color references are primarily to the R.H.S. Colour Chart of The Royal Horticultural Society of London.

THE PLANT

Classification:
- *Botanical.*—*Pelargonium×hortorum.*
- *Commercial.*—Zonal Florists Geranium.

Form: Bush; uniform mound.

Height: 20–22 cm above media surface.

Growth: Free and early flowering basal branching; vigorous, upright habit.

Strength: Stands upright without artificial support.

Foliage: Stalked leaf attachment; zoning present.

Leaves:
- *Size.*—6.5–9 cm across (fully expanded leaf).
- *Shape.*—Reniform; cordate base.
- *Margin.*—Crenate.
- *Texture.*—Leather and slightly pubescent.
- *Color.*—Top: Green Group 137C zone. Zone: Green Group 134A. Bottom: Yellow-Green Group 146B.
- *Ribs and veins.*—Palmate venation; Yellow-Green Group 147C.

Petioles: 3.5–8.0 cm in length; Color Yellow-Green Group 146C.

Stem:
- *Color.*—Yellow-Green Group 146C.
- *Internodes.*—1.5 cm-4.5 cm in length.

THE BUD

Shape: Cluster is hemispherical; individual bud is pointed and ovoid.

Size: 1.5–2.0 cm across.

INFLORESCENCE

Blooming Habit: Semi-double; hemispherical.

Size: 8.5–10.5 cm across.

Borne: Umbel; floret on pedicel; pedicel on peduncle; 4.8 cm above foliage canopy.

Florets:
- *Form.*—Semi-double, flat to slightly cupped.
- *Color.*—Top: Red Group 43D with an undertone of white (streaking) through the petals. Bottom: Red Group 48C.

Petals: Obovate; separate, not united; margin entire; flat to slightly cupped; 7 to 9 in number.
- *Size.*—4.0 to 4.5 cm across.

*Texture and appearance.*—Smooth and satiny. Appearance from a distance is a rich salmon color. It is only on close inspection that one notices the white.

Petaloids:

*Quantity.*—1 to 4 in number.

*Shape.*—Twisted.

*Color.*—Red Group 43D.

Pedicel:

*Length.*—2.5–3.0 cm in length.

*Color.*—Base: Yellow-Green Group 140C (peduncle end). Tip: Greyed-Purple Group 183B (stipule end).

Peduncle: Arises from the node, opposite leaf petiole.

*Color.*—Yellow-Green 146B.

*Length.*—10 to 16 cm.

Disease resistance: Not known.

Lasting quality: This variety has been gardened tested during the summers of 1987, 1988 and 1989 and has proven continuously to withstand both heat and rain.

REPRODUCTIVE ORGANS

Stamens:

*Anthers.*—2 mm in length; 5–7 in number.

*Filaments.* 6–7 mm in length; white to pale pink in color.

*Pollen.*—Golden brown.

Pistils:

*Number.* 1.

*Length.*—8–10 mm.

*Stigma.*—1; 5–6 parted, Red-Purple Group 58A.

*Style.*—1; 2–3 mm in length, Red-purple Group 58A.

Ovaries: Superior; pale green; very pubescent; 4–6 mm in length.

Fruit: None observed.

The new cultivar is characterized by its delicate salmon color against a medium green foliage. The plant habit is a compact bush habit providing an abundance of cuttings. It is further characterized by its lasting quality, free and early flowering, basal branching and vigorous and upright habit.

I claim:

1. A new and distinct variety of Geranium plant substantially as shown and described.

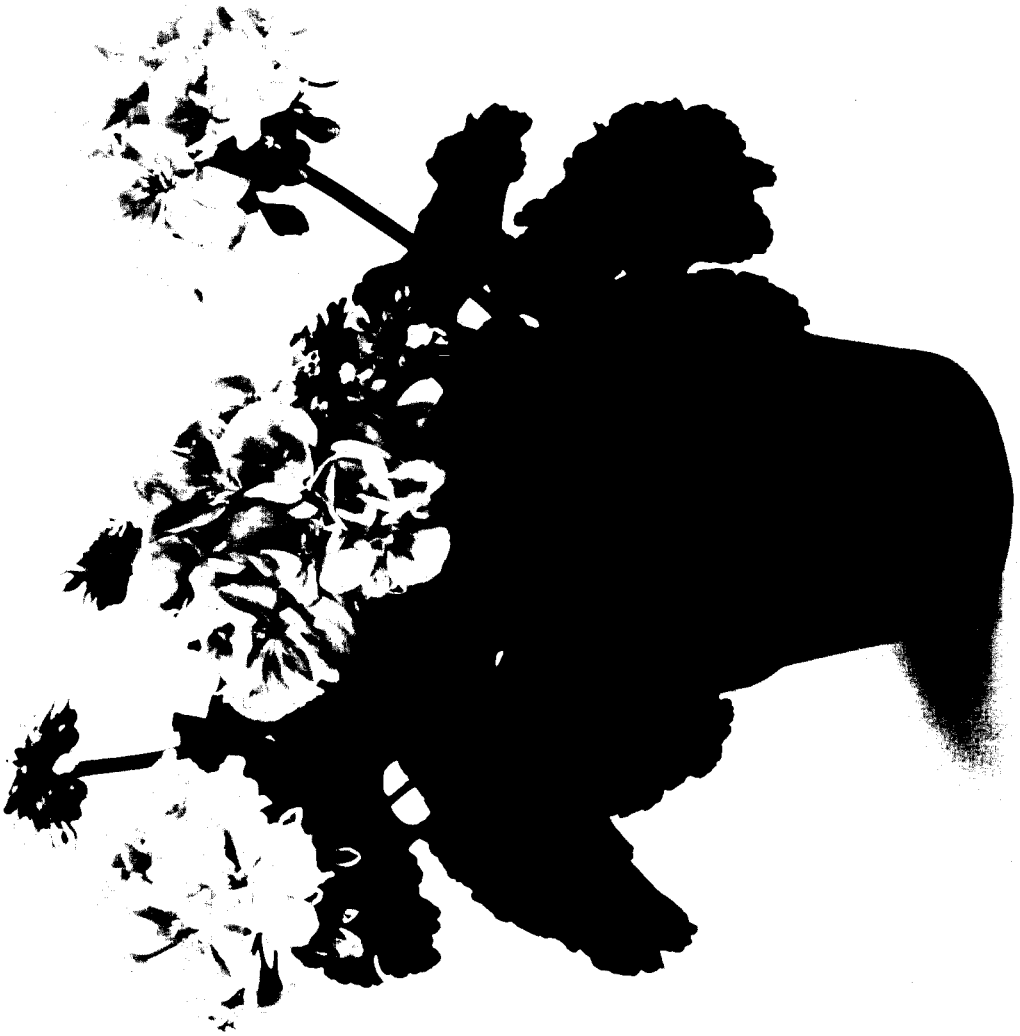

* * * * *